United States Patent
Tang et al.

(10) Patent No.: US 7,302,856 B2
(45) Date of Patent: Dec. 4, 2007

(54) STRAIN SENSORS BASED ON NANOWIRE PIEZORESISTOR WIRES AND ARRAYS

(75) Inventors: Hongxing Tang, Pasadena, CA (US); Michael L. Roukes, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 155 days.

(21) Appl. No.: 10/826,007

(22) Filed: Apr. 16, 2004

(65) Prior Publication Data

US 2005/0034529 A1    Feb. 17, 2005

Related U.S. Application Data

(63) Continuation-in-part of application No. PCT/US03/14566, filed on May 7, 2003, and a continuation-in-part of application No. PCT/US03/14284, filed on May 7, 2003, and a continuation-in-part of application No. PCT/US03/14286, filed on May 7, 2003.

(60) Provisional application No. 60/468,452, filed on May 7, 2003.

(51) Int. Cl.
*G01B 7/16* (2006.01)
(52) U.S. Cl. ..................................... 73/777
(58) Field of Classification Search .......... 73/777
See application file for complete search history.

(56) References Cited

U.S. PATENT DOCUMENTS 3,034,345 A * 5/1962 Mason ............. 73/862.623
4,798,206 A * 1/1989 Maddison et al. ......... 607/122
5,266,801 A 11/1993 Elings et al.
5,872,372 A * 2/1999 Lee et al. .................. 257/254
6,006,606 A * 12/1999 Shinogi et al. .......... 73/514.33
6,075,585 A 6/2000 Minne et al.
6,185,991 B1 2/2001 Hong et al.
6,784,074 B2 * 8/2004 Shchukin et al. ........... 438/412
6,823,717 B2 * 11/2004 Porter et al. ............... 73/31.05
6,882,051 B2 * 4/2005 Majumdar et al. ......... 257/746
6,887,365 B2 * 5/2005 Naughton .................. 205/104

(Continued)

FOREIGN PATENT DOCUMENTS

WO    WO 03/095616 A2    11/2003

(Continued)

OTHER PUBLICATIONS

Harley et al., "High-Sensitivity Piezoresistive Cantilevers Under 1000 A Thick," Physics Letters, vol. 75, No. 2, American Institute of Physics, Jul. 12, 1999, pp. 289-291.

(Continued)

*Primary Examiner*—Max Noori
(74) *Attorney, Agent, or Firm*—Foley & Lardner LLP

(57) ABSTRACT

A highly sensitive and ultra-high density array of electro-mechanical nanowires is fabricated. Nanowires are extremely sensitive to the strain induced by the attachment of biological and chemical species. Real-time detection is realized through piezoresistive transduction from the specially designed materials that form the nanowires. These specially designed materials include doped silicon or germanium, doped III-V semiconductors such as GaAs, GaN and InAs systems, and ultra-thin metal films.

26 Claims, 13 Drawing Sheets

U.S. PATENT DOCUMENTS

| | | | |
|---|---|---|---|
| 6,945,099 | B1 | 9/2005 | Su et al. |
| 7,159,448 | B2* | 1/2007 | Moelkner et al. ............ 73/35.12 |
| 2002/0166962 | A1* | 11/2002 | Roukes et al. ................ 250/306 |
| 2002/0174715 | A1* | 11/2002 | Kim et al. ...................... 73/105 |
| 2002/0175408 | A1 | 11/2002 | Majumdar et al. |
| 2002/0178801 | A1* | 12/2002 | Takahashi et al. ............. 73/105 |
| 2003/0062193 | A1 | 4/2003 | Thaysen et al. |
| 2003/0089182 | A1 | 5/2003 | Thaysen et al. |
| 2003/0135971 | A1* | 7/2003 | Liberman et al. ........... 29/419.1 |
| 2003/0203531 | A1 | 10/2003 | Shchukin et al. |
| 2005/0109925 | A1 | 5/2005 | El Rifai et al. |
| 2005/0150280 | A1 | 7/2005 | Tang et al. |
| 2005/0212529 | A1 | 9/2005 | Huang et al. |
| 2005/0214803 | A1* | 9/2005 | Wang .............................. 435/6 |
| 2005/0236357 | A1* | 10/2005 | Bakkers et al. ................. 216/2 |
| 2005/0244326 | A1* | 11/2005 | Colbert et al. ............ 423/447.1 |
| 2005/0275502 | A1* | 12/2005 | Goebel et al. ................. 338/42 |

FOREIGN PATENT DOCUMENTS

| | | |
|---|---|---|
| WO | WO 03/095617 A2 | 11/2003 |
| WO | WO 2004/041998 A2 | 5/2004 |

OTHER PUBLICATIONS

Harley et al., "1/F Noise Consideration for The Design and Process Optimization of Piezoresistive Cantilevers," Journal of Microelectromechanical Systems, vol. 9, No. 2, IEEE, Jun. 2, 2000, pp. 226-235.
Hutter et al., "Calibration of Atomic-Force Microscope Tips," Rev. Sci. Instrum., vol. 64, No. 7, American Institute of Physics, Jul. 1993, pp. 1868-1873.
Kuczynski, "Effect of Elastic Strain on The Electrical Resistance of Metals," Physical Reivew, vol. 94, No. 1, Apr. 1, 1954, pp. 61-64.
Li et al., "Thin Gold Film Strain Gauges," J. Vac. Sci. Technol., vol. 12, No. 3, American Vacuum Society, May 1994, pp. 813-819.
Parker et al., "Electrical Resistance-Strain Characteristics of Thin Evaporated Metal Films," Journal of Applied Physics, vol. 34, No. 9, Sep. 1963, pp. 2700-2708.
Physics Web, "Nanoelectromechanical Systems Face The Future," Physics World Magazine, vol. 14, Issue 2, Feb. 2001, http://physicsweb.org/article/world/14/2/8.
Reid et al., "6-MHz 2-N/m Piezoresistive Atomic-Force-Microscope Cantilevers With INCISIVE Tips," Journal of Microelectromechanical Systems, vol. 6, No. 4, IEEE, Dec. 4, 1997, pp. 294-302.
Thaysen et al., "Polymer-Based Stress Sensor With Integrated Readout," Journal of Physics D: Applied Physics, vol. 35, Institute of Physics Publishing Ltd., 2002, pp. 2698-2703.
Tortonese et al., "Atomic Resolution With An Atomic Force Microscope Using Piezoresistive Detection," Applied Physics Letters, vol. 62, No. 8, American Institute of Physics, Feb. 22, 1993, pp. 834-836.
Yang et al., "Monocrystalline Silicon Carbide Nanoelectromechanical Systems," Applied Physics Letters, vol. 78, No. 2, American Institute of Physics, Jan. 8, 2001, pp. 162-164.
Melosh et al., "Ultrahigh-Density Nanowire Lattices and Circuits," Science, Apr. 4, 2003, vol. 300, pp. 112-115.
Hrovat et al., "A characterisation of thick film resistors for strain gauge applications," J. Mater. Sci., 2001, vol. 36, pp. 2679-2689.
Knight et al., "Effect of Structure on the Piezoresistive Properties of Thin Metal Films," J. Vac. Sci. Technol., 6, 706-710, 1969.
Chung et al., "Micromachined metal thin-film pressure sensor suitable for batch process," Electronics Letters, Oct. 24, 2002, vol. 38, No. 22, 1344-1346.
Pattabi et al., "A simple strain cell for the measurement of gauge factor of a thin film," Rev. Sci. Inst., Apr. 1999, vol. 70, No. 4, pp. 2074-2075.
Bishay et al., "Applicability of discontinuous palladium films as strain gauges," J. Mater. Sci., 1992, vol. 3, pp. 195-199.
Jen et al., "Piezoresistance characteristics of some magnetic and non-magnetic metal films," J. Magn. Magn. Mater., 2003, vol. 256, pp. 54-62..
McGuire et al., "Anisotropic Magnetoresistance in Ferromagnetic 3d Alloys," IEEE Trans. Mag-11, Jul. 4, 1975, No. 4, pp. 1018-1038.
Rajanna et al., "Pressure transducer with Au—Ni thin-film strain gauges," IEEE Trans. Electron Devices, Mar. 1993, vol. 40, No. 3, pp. 521-524.
Sampath et al., "Behaviour of Bi—Sb alloy thin-film strain gauges," Thin-Solid Films, 1986, 137, pp. 199-205.
Chiriac et al., "Ni—Ag thin films as strain-sensitive materials for peizoresistive sensors," Sensors and Actuators A, 1999, vol. 76, pp. 376-380.
Lei et al., "Thin film thermocouples and strain gauge technologies for engine applications," Sensors and Actuators A, 1998, vol. 65, pp. 187-193.
Guckel et al., "Surface micromachined pressure transducers," Sensors and Actuators A, 1991, vol. 28 (2), pp. 133-146.
Patridge et al., "High-performance planer peizoresistive accelerometer," JMEMS, Mar. 1, 2000, vol. 9, No. 1, pp. 58-66.
Chui et al., "Independent detection of vertical and lateral forces with a sidewall-implanted dual-axis piezoresistive cantilever," Appl. Phys. Lett., Mar. 16, 1998, vol. 72, No. 11, pp. 1388-1390.
Dehe et al., "A piezoresistive GaAs pressure sensor with GaAs/AlGaAs membrane technology," J. Micromech. Microeng., 1995, vol. 5, pp. 139-142.
Hsu et al., "Piezoresistive response induced by piezoelectric charges in n-type GaAs mesa resistors for application in stress transducers," J. Appl. Phys. Jan. 1, 1999, vol. 85, No. 1, pp. 333-340.
Tang et al., "Two-dimensional electron-gas actuation and transduction for GaAs nanoelectromechanical systems," Appl. Phys. Lett. Nov. 11, 2002, vol. 81, No. 20, pp. 3879-3881.
Konczewicz et al., "GaAlAs-Based Micromachined Accelerometer," Phys. Stat. Sol. B, 2001, vol. 223, pp. 593-596.
Bykhovski et al., "Piezoresistive effect in wirtzite n-type GaN," Appl. Phys. Lett. Feb. 5, 1996, vol. 68, No. 6, pp. 818-819.
Gaska et al., "Piezoresistive effect in GaN-AlN-GaN structures," Appl. Phys. Lett., Dec. 29, 1997, vol. 71, No. 26, pp. 3817-3819.
Gaska et al., "Piezoresistive effect in AlN/GaN short range superlattice structures," J. Appl. Phys. May 1, 1999, vol. 85, No. 9, pp. 6932-6934.
Harley et al., "High-sensitivity piezoresistive cantilevers under 1000 Å thick," Appl. Phys. Lett., Jul. 12, 1999, vol. 75, No. 2, pp. 289-291.
Mosser et al., "Energy shifts due to the local environment of DX centers in $Al_xGa_{1-x}As$:Si," Mater. Sci. Forum, 1994, vols. 143/147, pp. 1117-1122.
Eickhoff et al., "Piezoresistivity of $Al_xGa_{1-x}N$/GaN heterostructures," J. Appl. Phys. Oct. 1, 2001, vol. 90, No. 7, pp. 3383-3386.
Van Vessem et al., "Rediscovering the Strain Gauge Pressure Sensor," Sensors online, vol. 16, No. 4, 6 pgs., Apr. 1999.

* cited by examiner

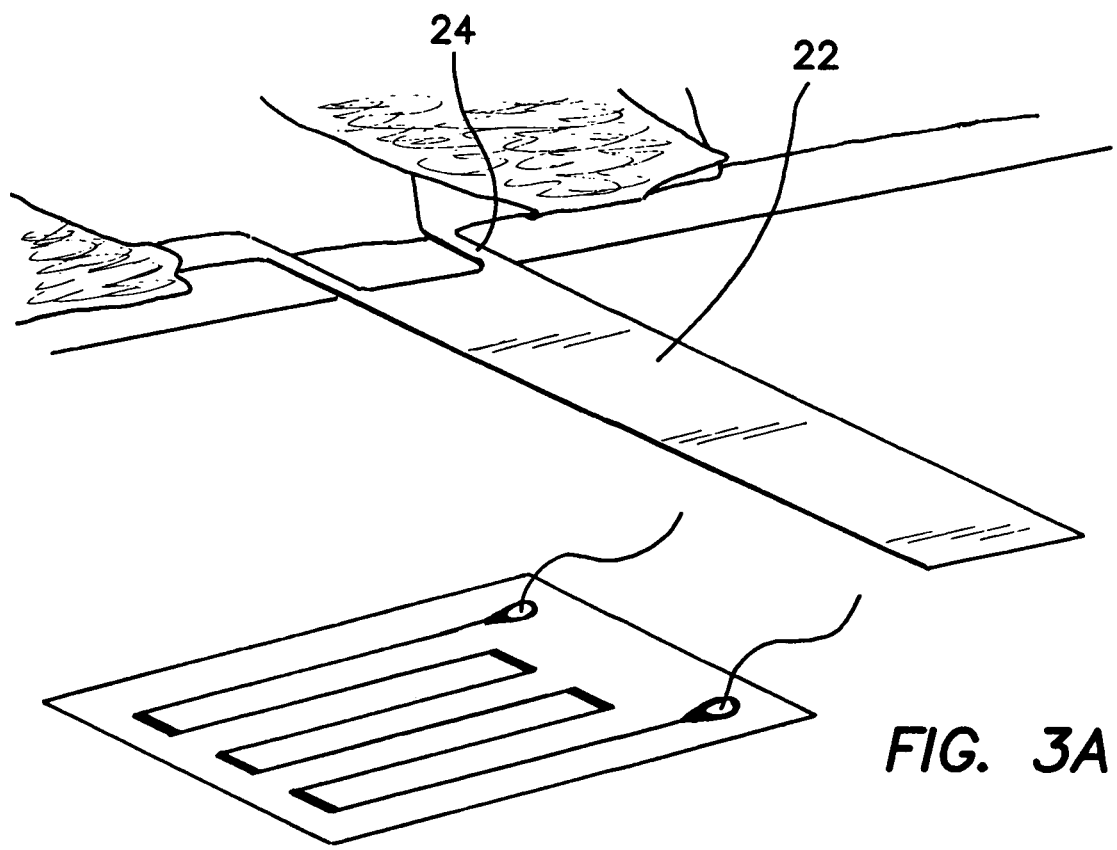
FIG. 3A
FIG. 3B
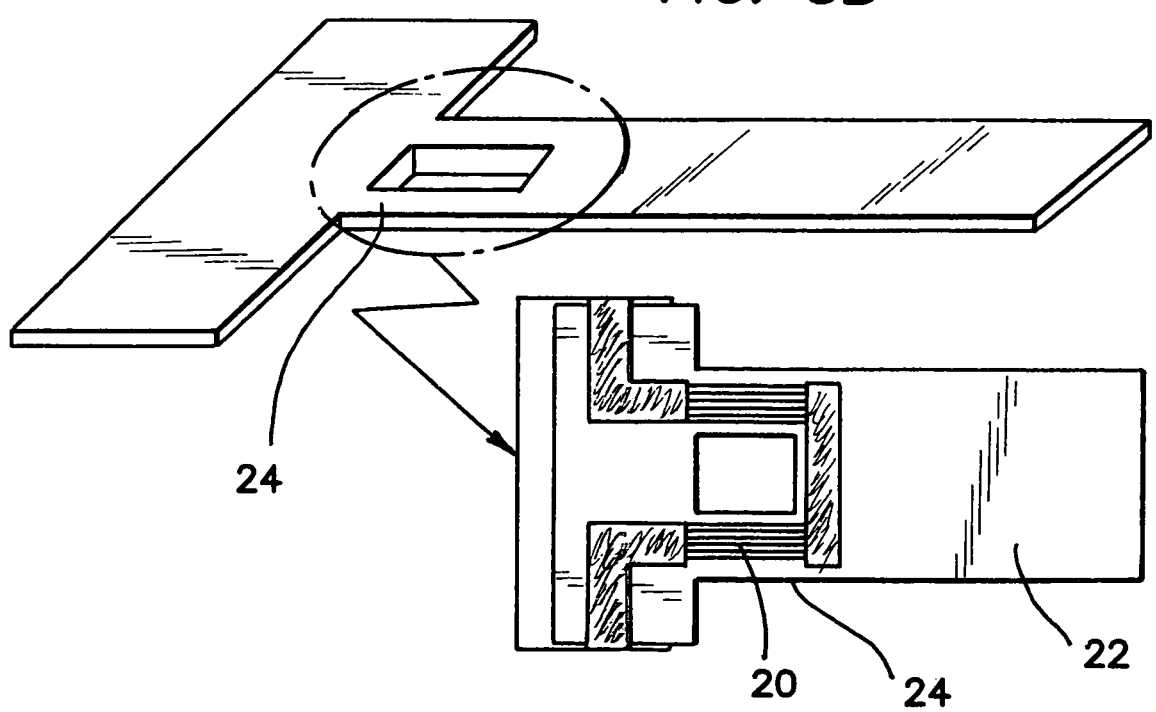

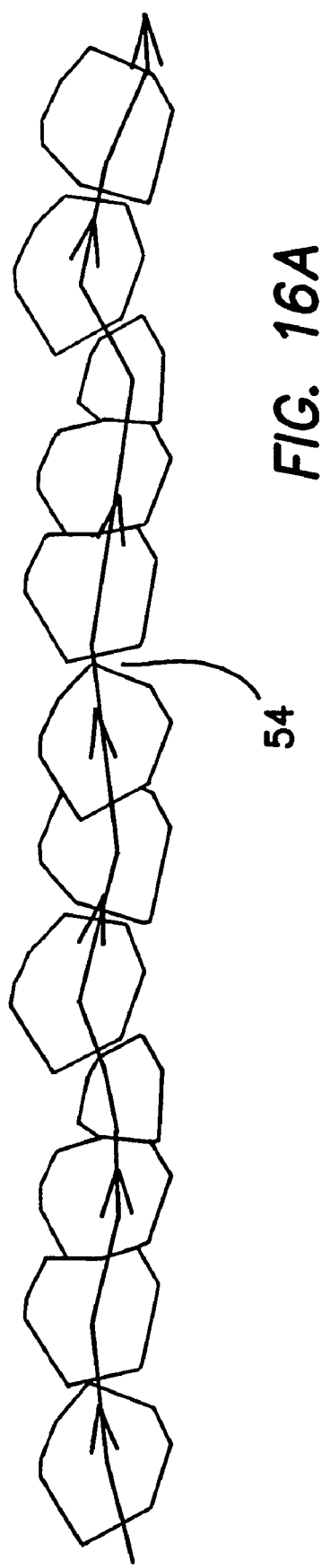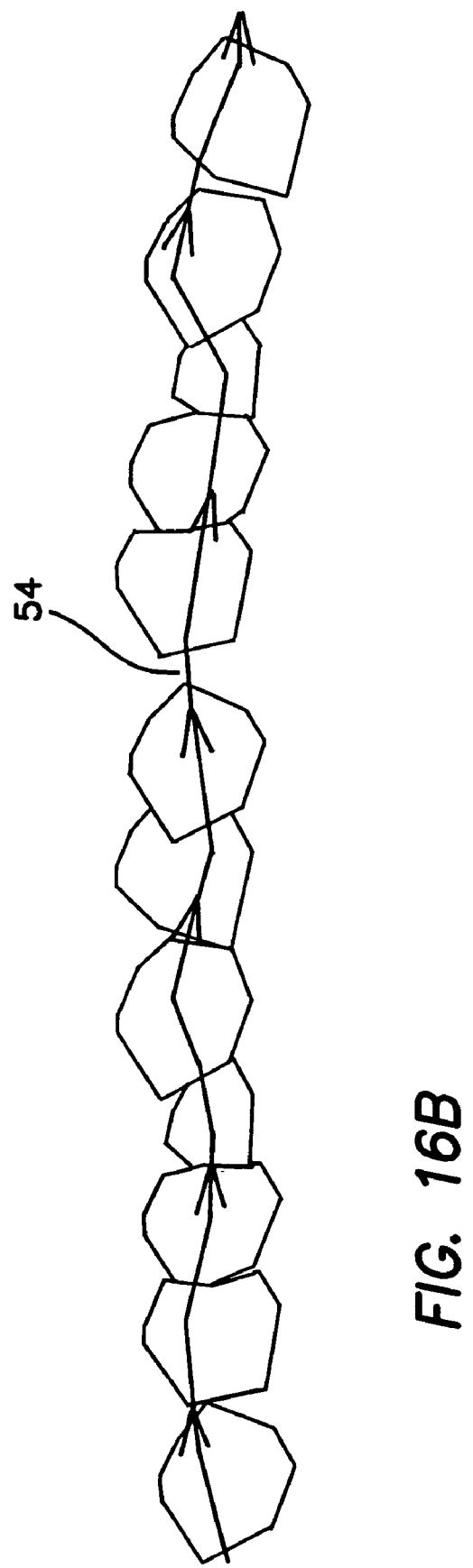
FIG. 16A
FIG. 16B

STRAIN SENSORS BASED ON NANOWIRE PIEZORESISTOR WIRES AND ARRAYS

RELATED APPLICATIONS

The present application is related to U.S. Provisional Patent Application Ser. No. 60/468,452, filed on May 7, 2003, to which priority is claimed pursuant to 35 USC 119, and is a continuation-in-part application of PCT Patent Applications serial no. PCT/US03/14566, PCT/US03/14284, and PCT/US03/14286, all filed on May 7, 2003, to which priority is claimed pursuant to 35 USC 120, 371 all of which applications are incorporated herein by reference.

The U.S. Government has certain rights in this invention pursuant to Grant No. ECS-0089061, awarded by the Nation Science Foundation (NSF); Grant No. F49620-02-1-0085, awarded by the United States Air Force Office of Sponsored Research (AFOSR); and Grant No. DABT63-98-1-00012 awarded by Defense Advanced Research Projects Agency (DARPA).

BACKGROUND OF THE INVENTION

1. Field of the Invention

The invention is directed to the field of electromechanical piezoresistive nanowire arrays, and in particular nanowire arrays fabricated with doped silicon or germanium, doped III-V semiconductors such as GaAs, GaN and InAs systems, and ultra-thin metal films and used for real-time detection of biological and chemical analytes.

2. Description of the Prior Art

Quantification of Piezoresistors

Fundamentally, all strain gauges are designed to convert mechanical motion into an electronic signal. A piezoresistor is basically a device which changes its resistance when strained. The change in resistance is proportional to the strain experienced by the sensor. The strain sensitivity, which is also called the gage factor (GF), is given by:

$$GF = \left(\frac{\Delta R}{R}\right) / \left(\frac{\Delta L}{L}\right) = \left(\frac{\Delta R}{R}\right) \text{Strain} \quad (1)$$

where R is the resistance, and L the length of the piezoresistor. There are two components of the piezoresistive effect in most materials: (1) the geometric component and (2) the resistivity components.

When a conducting wire is stretched, it becomes longer and thinner. Its resistance increases according to the Ohm's law. A good example of geometric effect is the liquid strain gauge, such as those made of mercury. When compressed, a tube of mercury becomes shorter in length and larger in diameter to maintain a constant volume. The resistance of such a strain gauge is given by $$R = \frac{\rho L}{A} = \frac{\rho L^2}{V} \quad (2)$$

where $\rho$ is the resistivity, A is the cross sectional area, L is the length and V the volume of the strain gauge.

Therefore, $$GF = \left(\frac{dR}{R}\right) / \left(\frac{dL}{L}\right) = 2 \quad (3)$$

This means that all liquid gauges have a gauge factor of 2, since essentially all liquid medium is incompressible. Before replaced by solid stage strain gauge instruments, liquid gauges were extensively used in hospitals to monitor the fluctuations in blood pressure.

Metal wires can also be used as strain gauges. Normally metal cannot be treated as incompressible nor is its resistivity constant. The gauge factors can be expressed by following Ohm's law:

$$R = \rho L / A \quad (4)$$

$$dR/R = d\rho/\rho + dL/L - dA/A$$

$$GF = \frac{dR/R}{dL/L} = 1 + 2v + \frac{d\rho/\rho}{dL/L}$$

In the above, v is defined as Poisson's ratio $$-\frac{dA/A}{2dL/L}.$$

For different metals, this quantity depends on the material mechanical properties as well as the conduction mechanism. In general metals have gauge factors between 2 and 4.

In equation (3) above, the first component of the gauge factor is a pure geometrical mechanism, but piezoresistive sensing usually refers specifically to strain gauges in semiconductors, whose conducting band changes in response to stress. Some doped semiconductors have a gauge factor over 100 times greater than those attributable to geometric changes alone.

| | Gauge Factor |
|---|---|
| | $GF = \frac{dR/R}{dL/L}$ |
| Type | GF |
| Metal foil | 1 to 5 |
| Thin-film metal | ~2 |
| Semiconductor | 80 to 150 |
| Diffused semiconductor | 80 to 200 |

BRIEF SUMMARY OF THE INVENTION

The invention is shown in the illustrated embodiment as a nanowire strain gauge comprising a piezoresistive wire having a cross sectional area of the order of 100 nm×100 nm or less and a means for measuring resistance change in the piezoresistive wire in response to a transverse force applied to the piezoresistive wire.

In one embodiment the piezoresistive wire comprises a free standing nanowire clamped at opposing ends. The nanowire strain gauge may further comprise a biofunctionalized element suspended by and connected to the free standing nanowire.

In another embodiment the nanowire strain gauge further comprises a flexure element and the piezoresistive wire comprises an embedded piezoresistive wire in the flexure element. The flexure element comprises in one illustrated embodiment at least one arm in a notched nanocantilevers and preferably in a pair of such parallel arms. The piezoresistive wire may further comprise an array of piezoresistive wires embedded in the flexure element.

In a first example the piezoresistive wire comprises a thin metal film with a thickness of the order of tens of nanometers or less or of such thickness that it comprises a discontinuous metal island structure. Examples of such thin metal films comprise a pure metal selected from the group consisting of Au, Cr, Ag, Pd, Ni, Pt, Mn and alloys, Au—Ni, NiCr, Bi—Sb, Ag—Ni, Cu—Ni, and Pt—Cr.

The piezoresistive wire may also comprise a thin metal film included in a bimorph structure comprised of a top layer comprised of the thin metal film and a bottom layer comprised of a higher resistive metal layer than the top layer, a semiconductor layer or an insulating layer.

Still further the piezoresistive wire is composed at least in part of doped crystalline silicon, doped silicon carbide, doped GaAs, doped $Ga_xAl_{1-x}As$, where $0<x<1$ or a doped AlGaN/GaN, AlN/GaN/InN or GaN/AlN/GaN heterostructure.

The invention further comprises a method of manufacturing the nanowire strain gauge described above and the method of measuring stresses and strains at nanoscale dimensions.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 3a is a microphotograph of a notched silicon cantilever that can be used to detect piconanoscale biological forces.

FIG. 3b is a sketch of an integrated cantilever system with integrated nanowire piezoresistor array at its base.

FIGS. 16a and 16b are conceptual diagrams illustrating the discontinuous grain or island structure in an unstressed and stressed very thin metal film, respectively, which can be exploited in nanowire arrays to provide substantially enhance gauge factors.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Nanowire Piezoresistor Sensor Design

If we were to sense a longitudinal force applied along the piezoresistor, the fractional change in resistance is, $$\Delta R/R = GF*F/EA \quad (5)$$

where E is the Young's modulus, and F is the force applied along the piezoresistor. Clearly, in order to have a large change in resistance, we generally try to choose small diameters, a small Young's modulus and a large gauge factor when possible. In this sense, nanowire piezoresistors, having a cross sectional area of the order 100 $nm^2$ in contrast to that of $10^6$ $nm^2$ in a commercial piezoresistor, will have an enhanced resistance change by a factor of 10,000.

In illustrated embodiment, we address a strain gauge 10 that is sensitive to a transverse force. The expression for the resistance change with a transverse force load, F, is generally different from Eq. 5 above. We will consider two classes of nanowire devices: (1) free standing nanowires and (2) embedded nanowires.

a. Free Standing Nanowires

Figure 1:
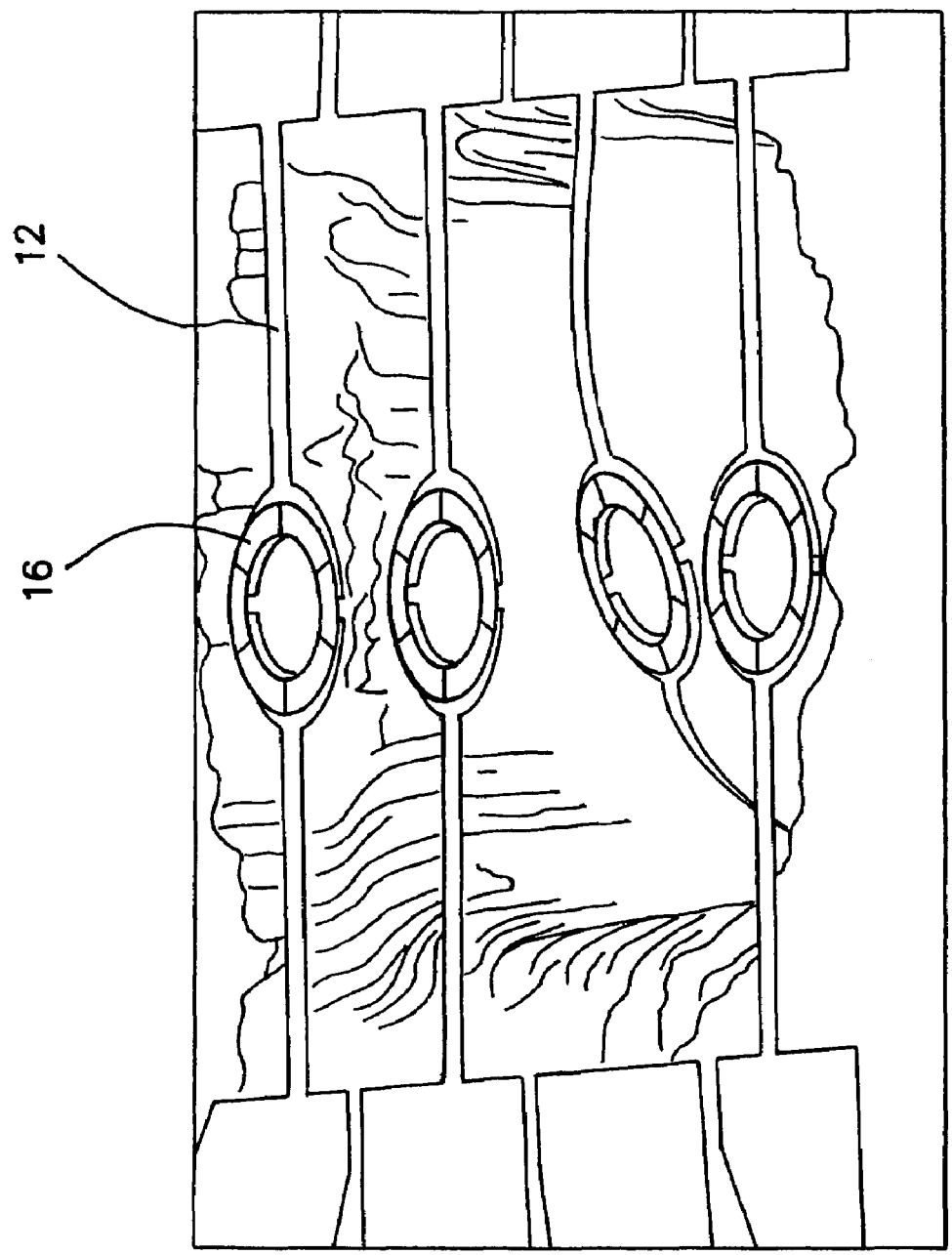
FIG. 1 is a microphotograph of a suspended nanowire with a circular element provided for carrying a biofunctionalized material.
Figure 8:
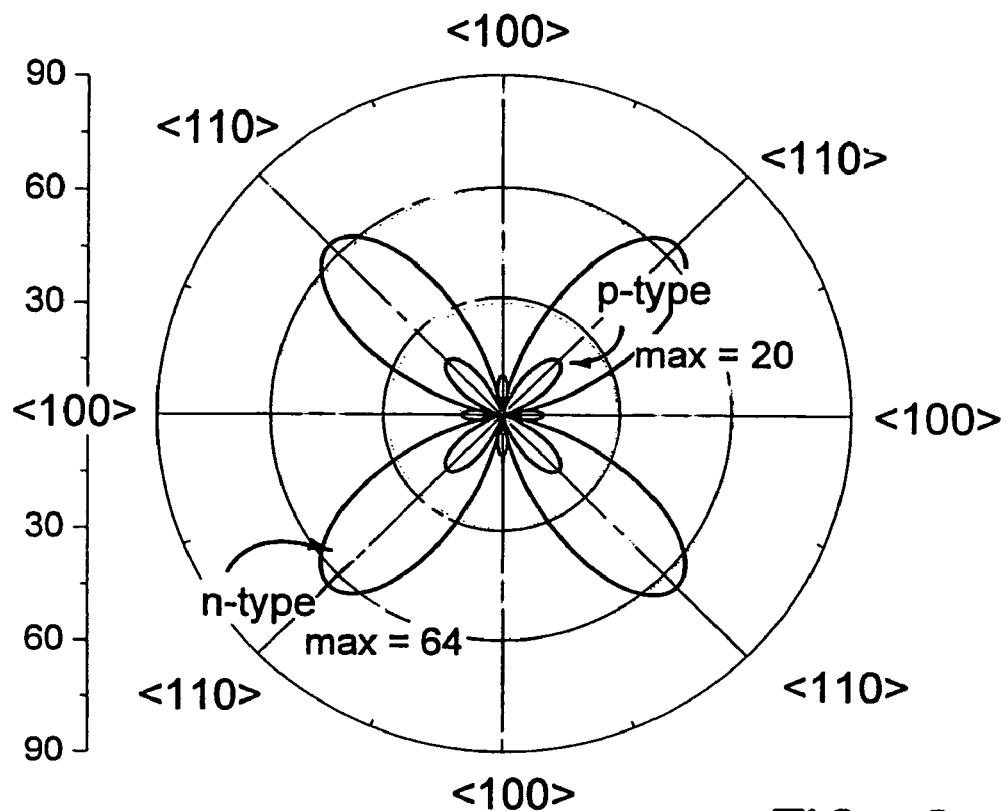
FIG. 8 is a polar graph of the room temperature piezoresistive coefficients of p-type and n-type Germanium on the (100) plane.

The free standing nanowires 12 are extremely small doubly clamped nanobeams as shown in FIG. 1. The analysis of a beam, which is fixed at both opposing ends, is similar to that of cantilever, which is fixed only at one end. For a bimorph beam of dimension l×w×t comprised of a layer of piezoresistor 14 of thickness $t_s$, best illustrated in FIG. 8, a point force load at the center of the beam causes a resistance change of, $$\Delta R/R = F(12\pi_l l(t-t_s)/wt^3) \quad (6)$$

Here $\pi_l$ is the piezoresistive coefficient of the sensing material and is closely related to the gauge factor. A simple comparison between Eq. (6) and Eq. (5) shows that for freestanding nanowires 12, the piezoresistive sensitivity can be further improved to a factor of $10^6$.

A demonstrated version of these suspended beams or nanowires 12 has been fabricated by the inventors. A photograph of nanowires 12 is shown in FIG. 1. The center circular ring 16 is designed as a biological trap to which biological species can be attached after proper biofunctionalization.

The nanowires 12 shown in FIG. 1 are fabricated by the use of electron beam lithography. The achievable size of the beam or nanowire 12 is around 50 nm wide. By using conventional superlattice nanowire pattern transfer technique as described by N. A. Melosh, et. al. Science 300, 112, (2003) suspended beams or nanowires 12 less than 10 nm size can be realized.

Figure 2:
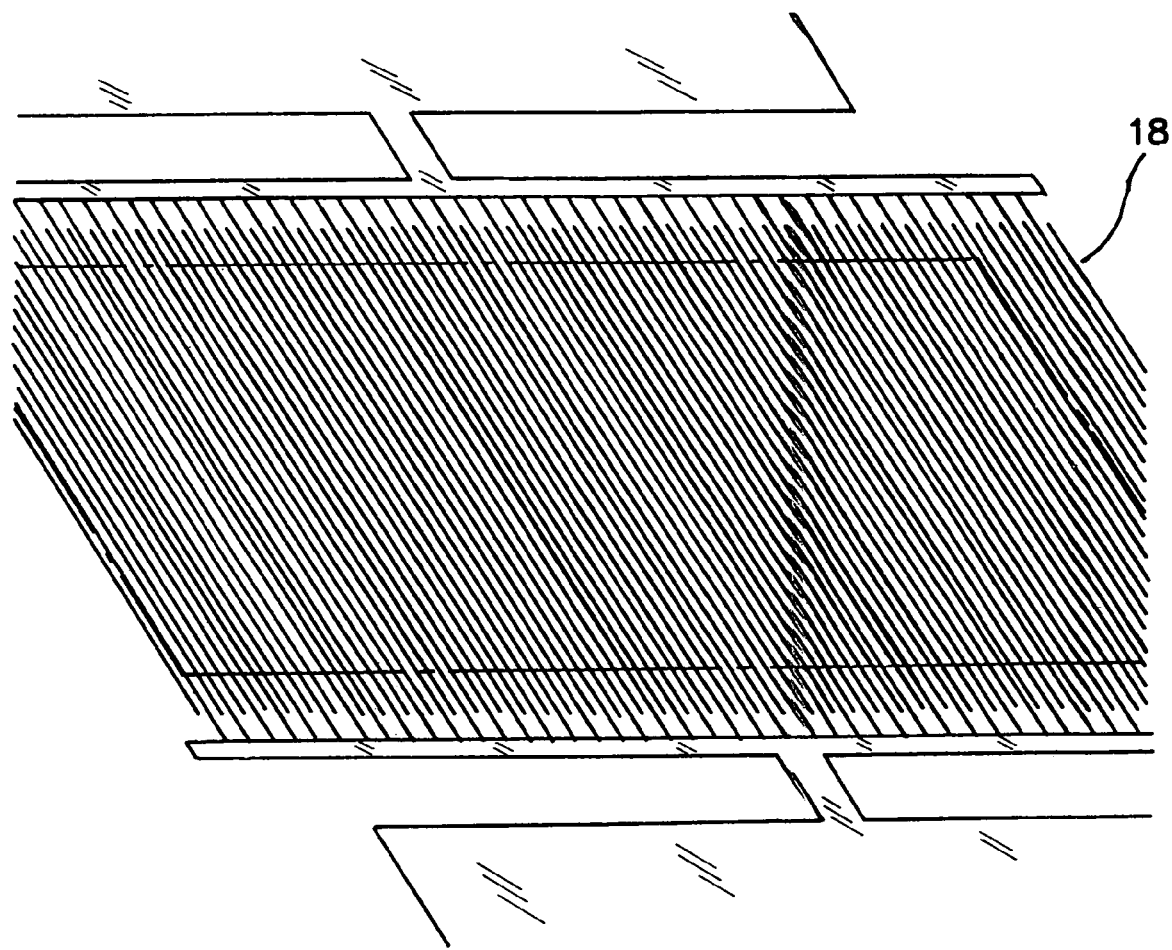
FIG. 2 is an array of piezoresistive nanowires.

FIG. 2 is a photograph of an interdigitated nanowire array 18 fabricated by electron beam lithography. In a nanowire piezoresistor array 18, the metal wires 12 are replaced by piezoresistive materials, such as doped Si, GaAs and or other piezoresistive materials.

b. Embedded Nanowires

Due to the difficulty of maintaining a finite conductivity in a nanoscale suspended semiconductor, we also propose a second type sensor design based on nanowire piezoresistors. In PCT Patent Applications serial no. PCT/US03/14566, PCT/US03/14284, and PCT/US03/14286, incorporated herein by reference, we have demonstrated a biofunctionized nanomechanical device that can realize ultra-sensitive and ultra-fast biochemical analysis. A notched cantilever 22 is used to detect biological forces applied on the biofunctionalized cantilever surface, i.e. a surface coated with a material which selectively binds to a biological analyte. An example of such a device is shown in FIG. 3a.

The scheme of embedded nanowire piezoresistor array 20 is illustrated in FIG. 3b, where arrays of nanowires are patterned above two arms 24 of the cantilever 22. The arms 24 of the cantilevers 22 act as an efficient strain concentrator and amplify the torque induced by biological species. The nanowires 12 can be laid out in parallel circuit as shown in FIG. 3b at the base of the cantilever 22 or in a serpentine serial circuit as shown in the inset in FIG. 3a.

The above mentioned stress changes can be picked up in the integrated piezoresistor. The relative change in resistance can be written as, $$\Delta R/R = -4 \cdot GF \cdot \sigma_s/Et \quad (8)$$

where E is Young's modulus for the piezoresistive material, t is the thickness of the piezoresistive material and $\sigma_s$ is the surface stress applied to a flexure element in which the wire is embedded.

Nanowire Fabrication—An Example

To provide a simple example how the nanowire array 18 is fabricated, an example is presented below. It is to be understood that many variations in the method described here can be practiced without departing from the principle of the disclosed invention.

Figure 10:
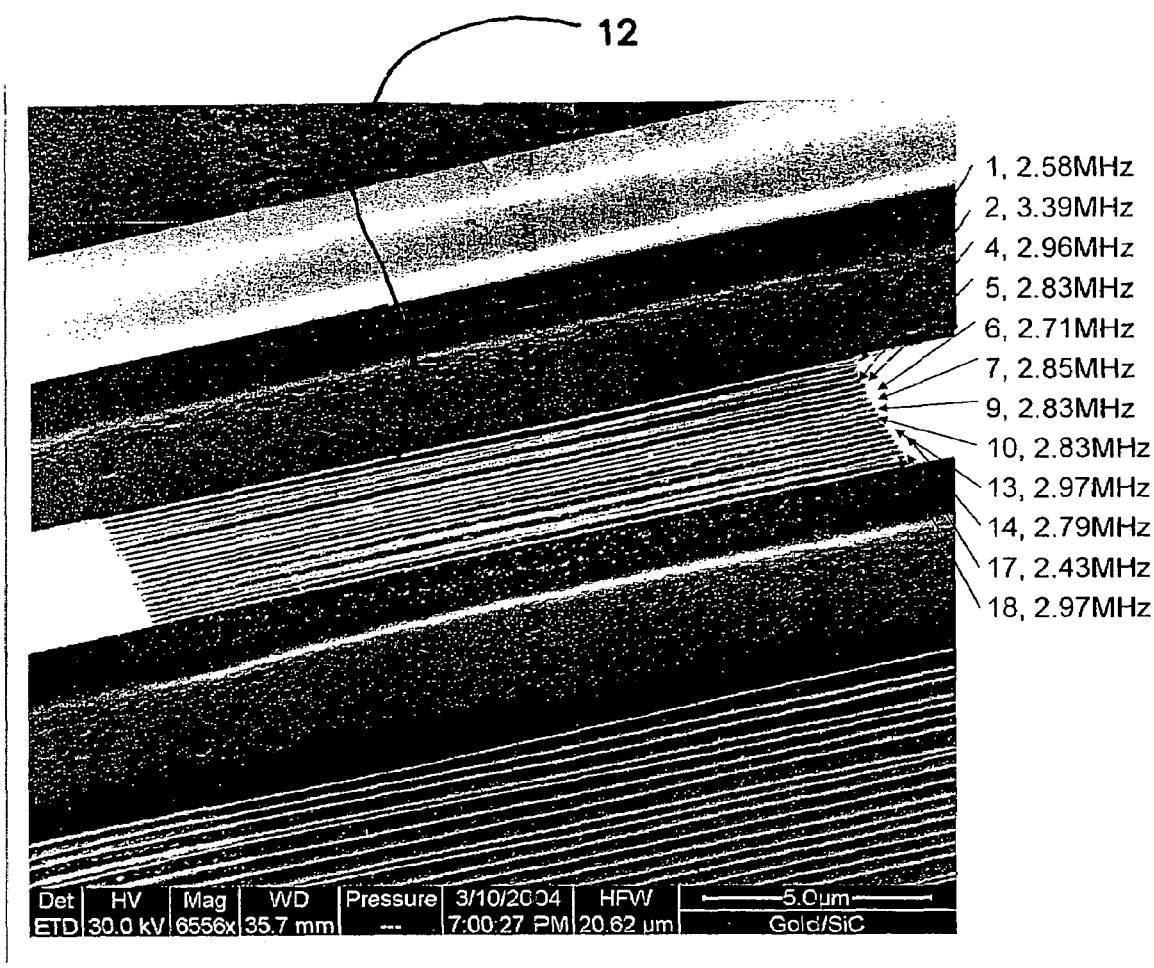
FIG. 10 is a scanning electron microscopic photograph of an array of nanowires fabricated according to the invention in which the resonant frequencies of 18 different wires are measured and indicated.
Figure 11A:
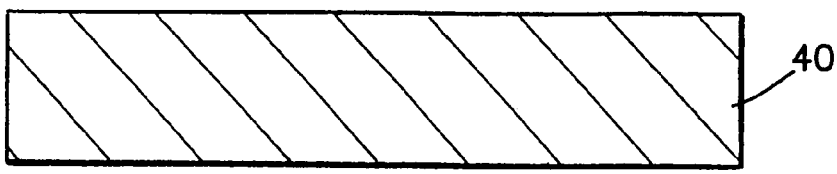
FIGS. 11a-11f is a process diagram of the method whereby the array of FIG. 10 can be made.
Figure 11B:
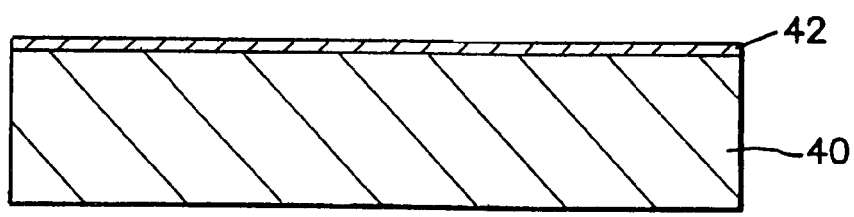
Figure 11C:
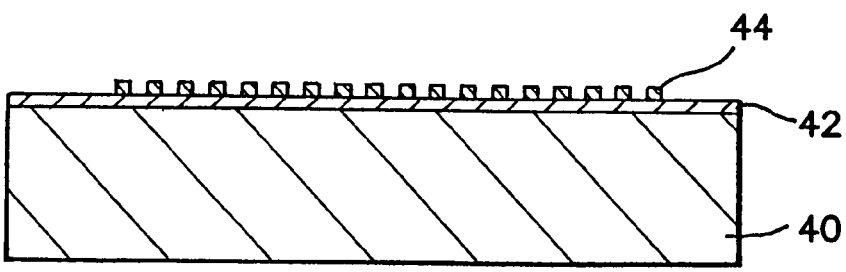
Figure 11D:
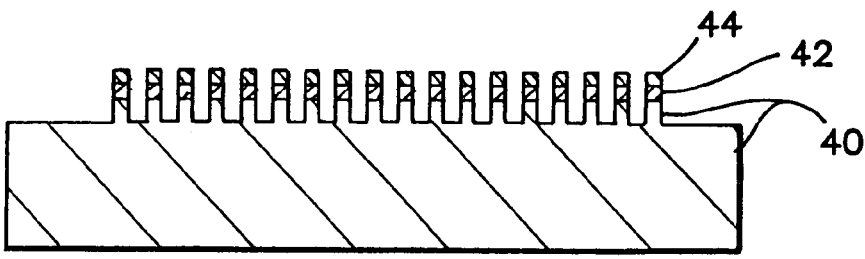
Figure 11E:
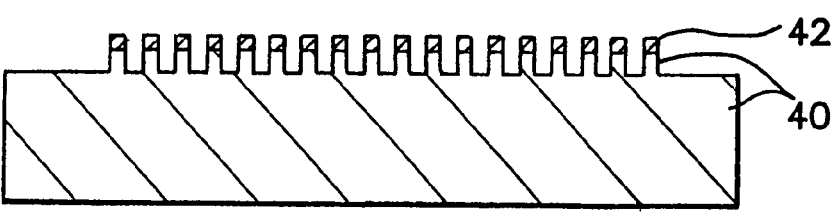
Figure 11F:
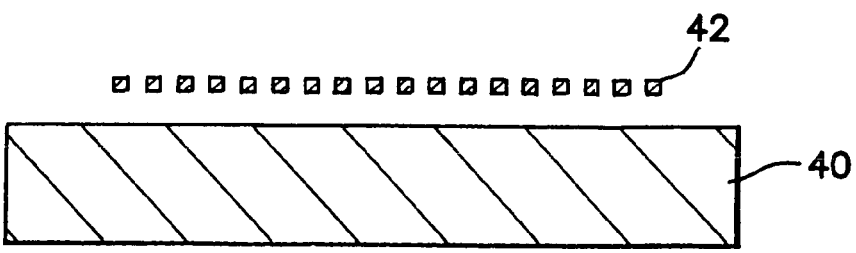
Figure 12:
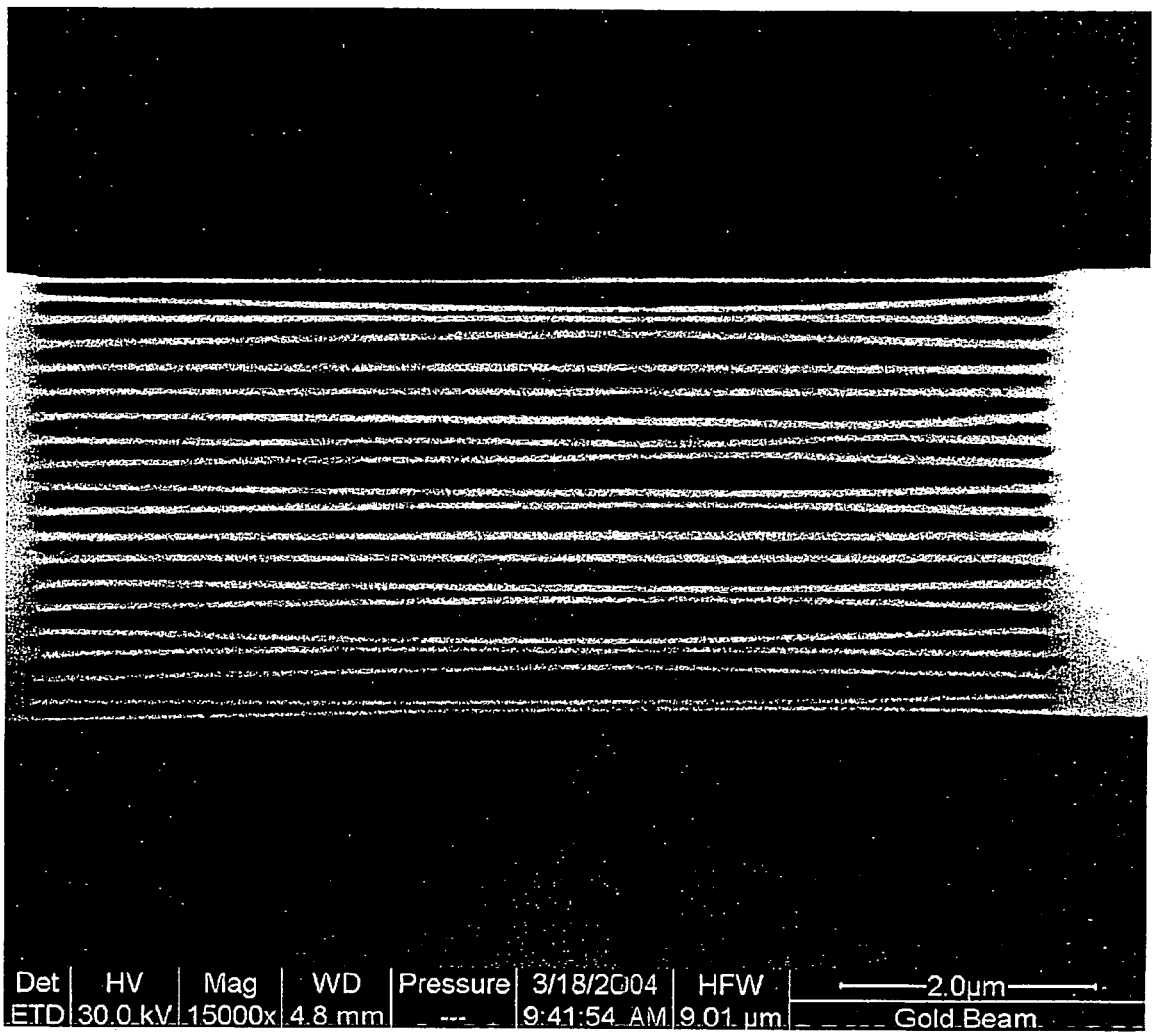
FIG. 12 is a magnified scanning electron microscopic photograph of an array of nanowires fabricated according to the invention.

FIG. 10 is a perspective SEM image of nanowire array 18 fabricated by means of top-down electron beam lithography. The wires 12 are made of Cr/Au and have a dimension of 20 μm long, 50 nm wide and 50 nm thick. A cross sectional view of the nanowire fabrication process is sketched in FIGS. 11a-11f. In FIG. 11a a bare silicon wafer 40 is provided. A layer 42 of Cr/Au is first evaporated on a silicon wafer 40 as shown in FIG. 11b. A FOX resist 44 is then spun on top of Cr/Au surface 42, followed by electron beam exposure of nanowire patterns to provide the patterned deposition of the resist as shown in FIG. 11c. After the development, the remaining FOX pattern 44 is employed as etch mask in an ion-milling instrument to remove Cr/Au 42 exposed between resist elements 44. The pattern in FOX is therefore transferred in to Cr/Au layer 42 and partially defined into wafer 40 as shown in FIG. 11d. FOX resist 44 is then removed in the step of FIG. 11e and a final isotropic silicon etch is used as shown in FIG. 11f to suspend Cr/Au beams 42 as wires 12. FIG. 12 is a SEM photograph of the top view of nanowire array 18 fabricated according to the method illustrated in FIGS. 11a-11f in which array 18 is shown as an 8 μm long array.

In-Situ Electron Beam Characterization of Nanowire Resonator

It should be clear that stresses and strains are not merely measured statically using nanowires 12, but also dynamically as a function of time. Hence, various types of nanostructures may incorporate or be coupled to the nanowires 12 of the invention and the piezoresistivity of nanowires 12 may be measured as a function of time, namely frequency spectrums of the piezoresistivity are obtained. For example, the scale of nanowires 12 is such that thermal fluctuations or thermal molecular motions in the gaseous or fluidic environment in which nanowires 12 are immersed are large enough to oscillate or displace nanowires 12. The nanowires 12, being the equivalent of mechanical strings, or taking on the mechanical characteristics of whatever nanostructure in which they are incorporated or to which they are coupled, will have one or more resonant frequencies responsive to the thermal fluctuations or thermal molecular motions, or to whatever other force may be present.

In order to explore the piezoresistivity of nanowires 12, it is important to know the resonant frequency of the nanowires 12 through other methods. This will provide a narrow frequency range to search for the resonant peak when piezoresistive detection is employed.

Figure 13:
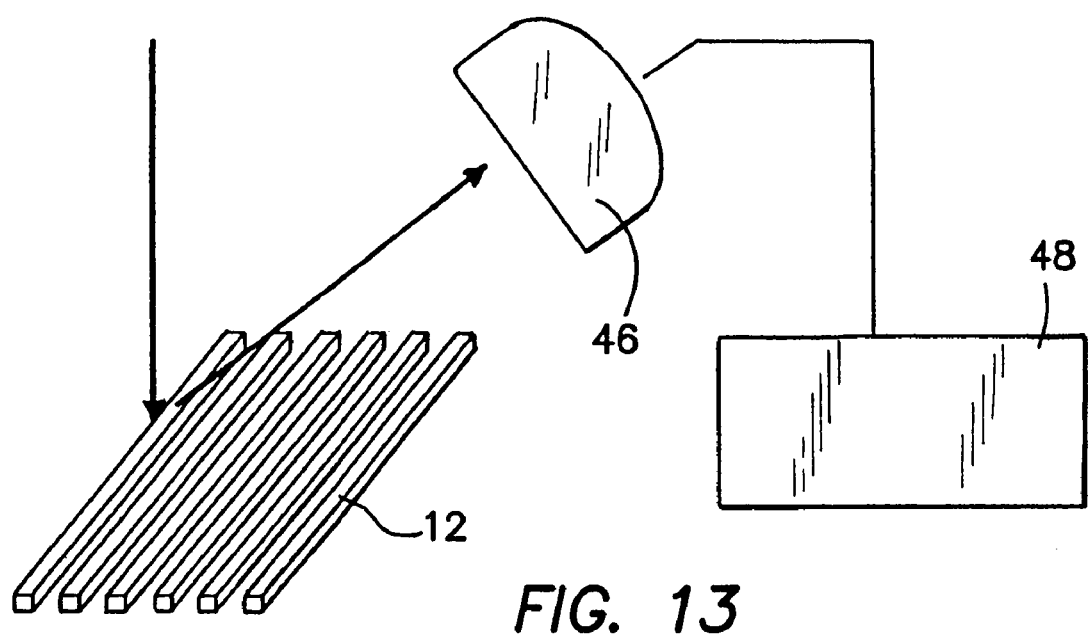
FIG. 13 is a diagram showing the means by which the measure of the resonant frequencies of the nanowires in the array are individually measured using an electron beam.
Figure 15:
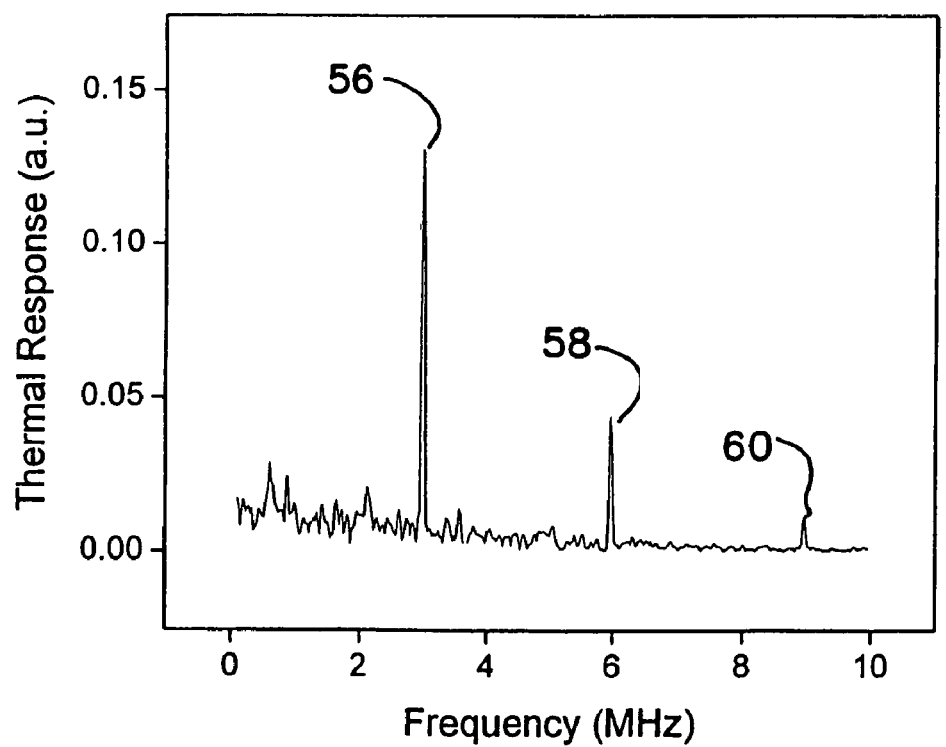
FIG. 15 is a graph of thermal response verses frequency showing measurement of higher harmonic modes of a nanowire in an array.
Figure 14A:
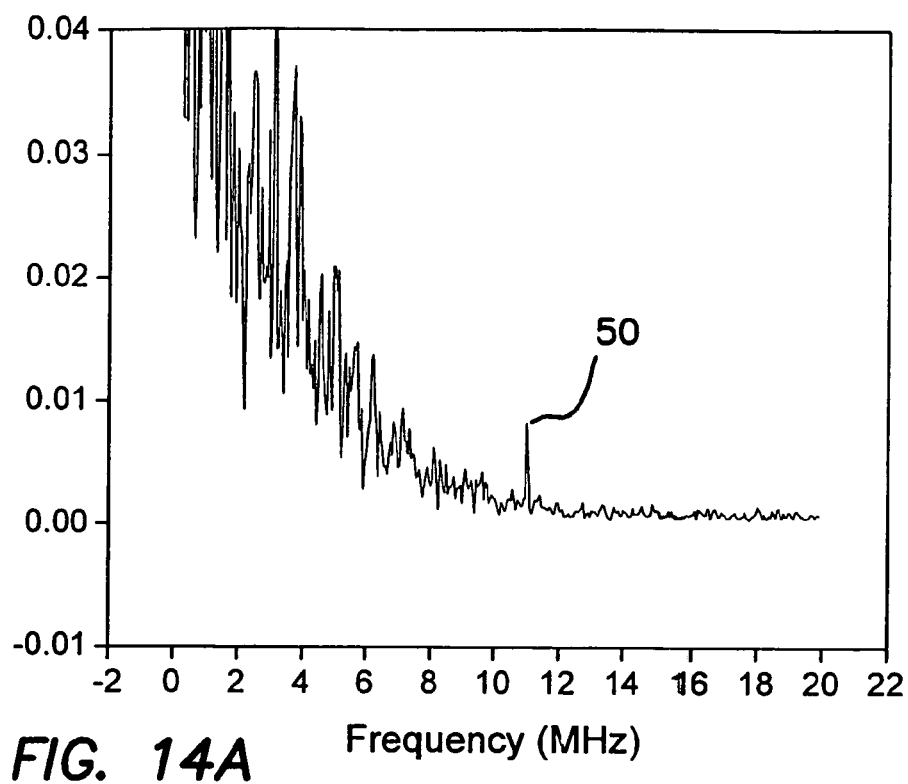
FIGS. 14a and 14b are graphs of thermal response verses frequency showing the resonant spectrum of two different nanowires in the array.
Figure 14B:
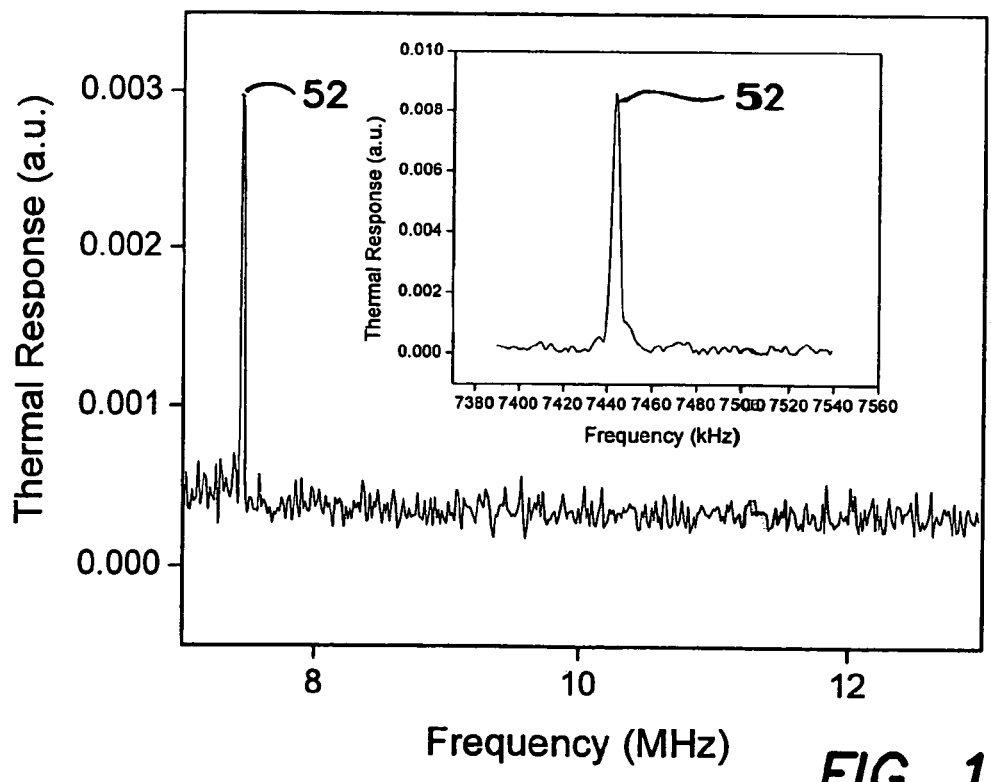

An in-situ electron beam detection has been proved to be very useful for this purpose. The measurements are performed at room temperature within a conventional, commercially available scanning electron beam microscope (SEM) as diagrammatically depicted in FIG. 13. Thermal excitation of nanowires 12 will drive them in motion at their respective resonant frequencies. An electron beam is focused on the edge of the target nanowire 12. When the electron beam is focused on a spot on the nanowire 12, the motion of the nanowire 12 will affect the signal detected in a secondary electron detector 46 (SE) or backscatter electron detector 46 (BSE). This signal can be detected by a spectrum analyzer 48 or an oscilloscope equipped fast Fourier transform (FFT) program. The video signal from detector 46 has a band width greater than 10 MHz in most commercial SEM. Therefore, a resonant frequency more than 10 MHz can be detected. In FIG. 14a, which is a graph of the thermal response in atomic units verses frequency, a resonant frequency 50 as high as 11 MHz is observed for wire 12, for example a second wire in 8 µm long nanowire array 18. FIG. 14b is a graph of the thermal response in atomic units verses frequency, which shows the thermal resonant peak 52 of a wire 12 which is the twentieth wire in the same array 18 of nanowires 12. The inset of FIG. 14b illustrates the resonance peak 52 in a magnified view. The quality factor is about 1800. Due to the intrinsic high resolution of this method, higher harmonic modes of thermal mechanical motion can be measured. Data is shown in FIG. 15 which is a graph of the thermal response in atomic units verses frequency, and which is the measured result for the $18^{th}$ wire 12 in a 20 µm long nanowire array 18, showing a resonant peak 56 and two higher harmonic peaks 58 and 60.

This in-situ measurement can measure the resonant frequency of each individual wire 12 in a nanowire array 18 individually. Therefore it is extremely useful for characterizing a large array 18 of nanowires 12. Electrical connection to each individual wire 12 is not required for such a method. FIG. 10 lists the resonant frequencies of different wires 12 in the array 18 depicted there. This electron beam spectroscopy of a nanomechanical resonator can be applied to detect dynamic motion or static motion of a nanomechanical system of other configurations and geometries as well.

Material Aspect of Making Nanowire Piezoresistor Arrays

Consider now the materials that can be appropriately used to construct piezoresistive nanowires 12. Generally speaking, all conducting materials are piezoresistive, as we have explained above. We will discuss two categories of piezoresistors: (1) piezoresistors of geometrical effect and (2) piezoresistors with varying piezoresistivity.

(1) a. Metal Thin Film Piezoresistor

Figure 4A:
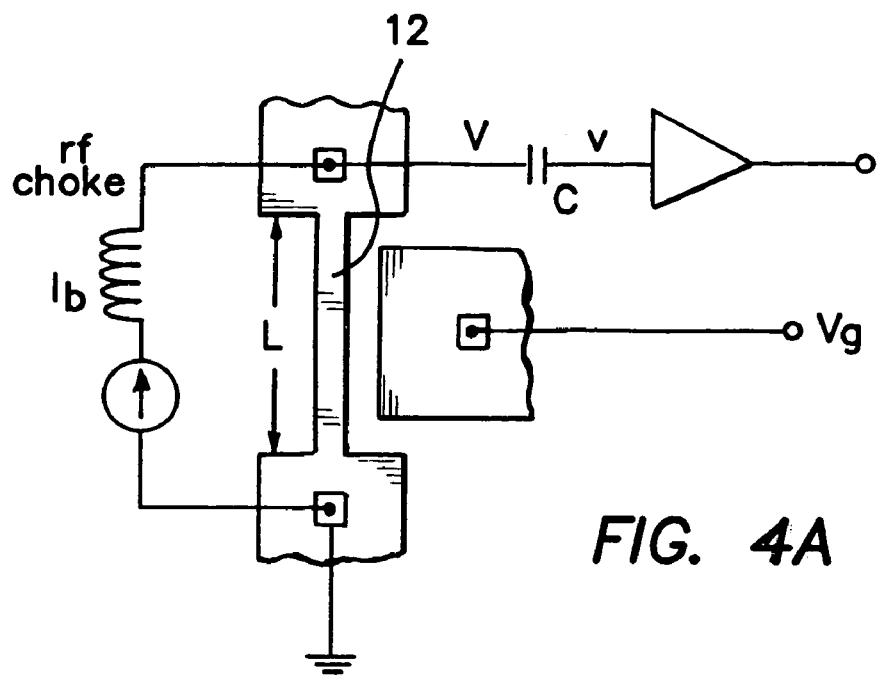
FIG. 4a is a diagram of a measurement circuit for integrated nanowire strain sensor.
Figure 4B:
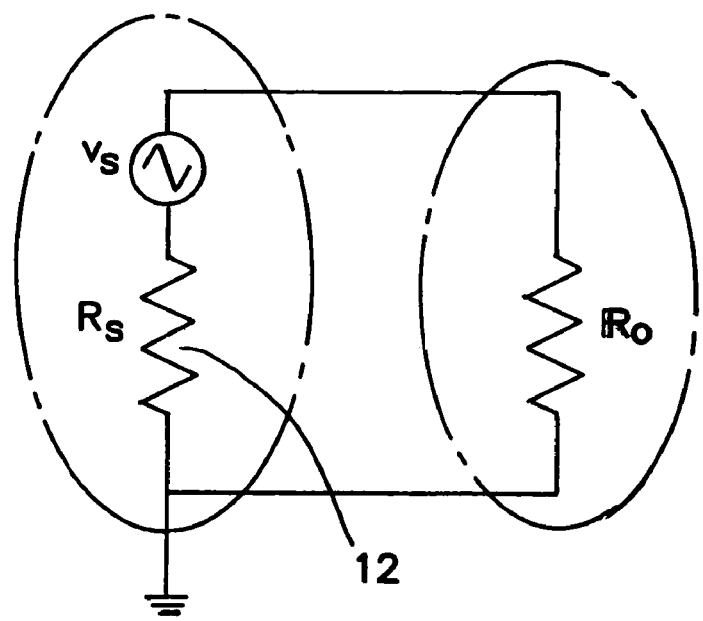
FIG. 4b is a schematic for an equivalent sensing circuit that is comprised of the nanowire resistance ($R_s$) and amplifier input resistance ($R_0$). The piezoresistive ac signal $Vs=I_b*GF*R_s$ is divided by the resistance network before amplification.
Figure 5A:
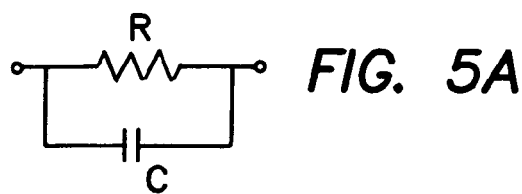
FIG. 5a is an equivalent circuit of an ultra-thin metal film nanowire strain sensor.
Figure 5B:
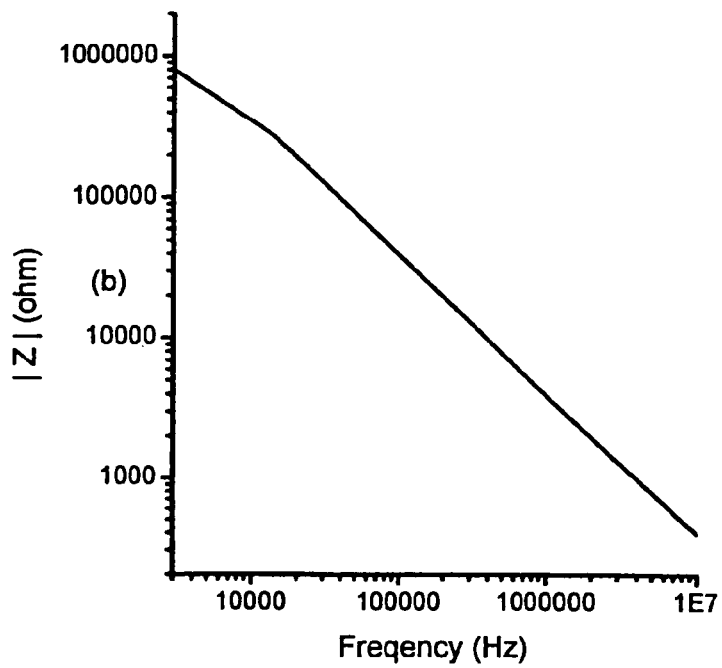
FIG. 5b is a graph of the Impedance |Z| vs frequency for a thin gold film of thickness of 5 nm.
Figure 5C:
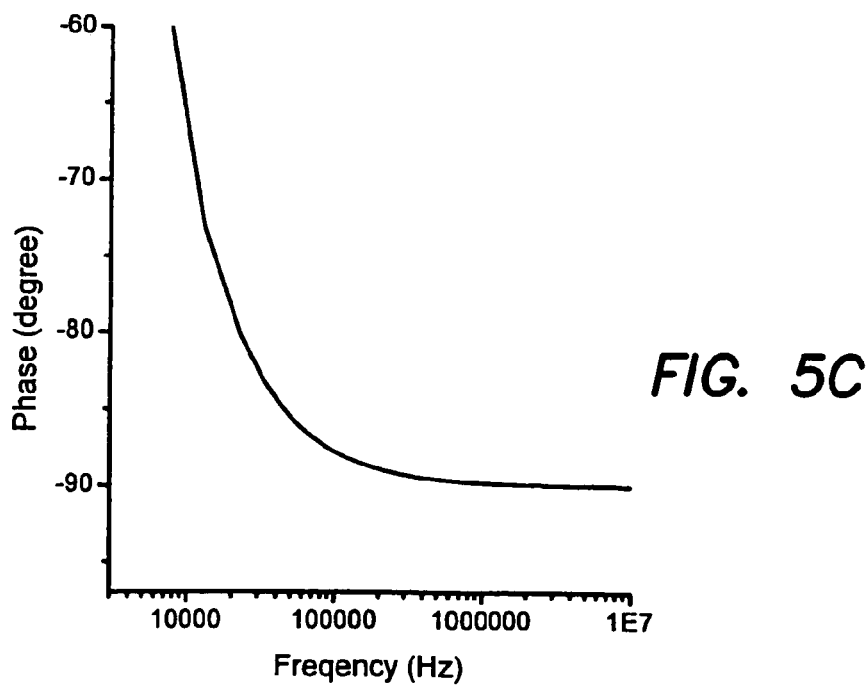
FIG. 5c is a graph of the phase angle vs frequency for a thin gold film of thickness of 5 nm.

Geometrical effect piezoresistors normally provide a smaller guage factor, nevertheless they represent a significant amount of materials used in commercial gauge sensors. These materials are mostly highly conductive thin metal films with very low resistivity. To obtain a larger change in the absolute value of resistance, a lot of effort has been expended to increase the resistance of the sensors. However, for high frequency applications, it is beneficial to maintain a low sensor resistance in order to match the resistance of the sensor with that of the measurement circuit, which is typically 50 Ω. FIG. 4a shows a representative measurement diagram. The signal appears at the input of the network analyzer or lock in amplifiers is, $$V = V_S \frac{R_0}{R_s + R_0} \quad (9)$$

Where $R_0$ is the input impedance of the measurement amplifier as shown in FIG. 4b and $R_S$ is thin film or nanowire resistance, and $V_s$ is the ac signal ($I_b \times GF \times R_s$) applied signal across the thin film with $I_b$ the bias current applied to the nanowire 12. The maximum signal power spectrum is transferred only when $R_s=R_0$. In this way, the transducer signal will not be significantly degraded. Normally the sheet resistance of semiconducting thin film is on the order of $10^2$ Ω to $10^3$ Ω. The two-terminal DC resistance of a high aspect ratio nanowire 12 could be $10^6$ Ω. This makes semiconducting nanowires 12 extremely difficult to be used as a sensing unit in high frequency mechanical resonator. On the other hand, the resistance of metal films can be easily trimmed to specific values by tuning the thickness of the film.

On the other hand, comparing to the resistive wires, the Johnson noise, $V_n = \sqrt{4\pi k T R_s}$, where k is the Boltzman constant, can be reduced by a factor of about 40. Therefore, the signal-to-noise ratio can be compensated even though the gauge factor is about 50 times weaker than for Si wires. The fact that metallic nanowires 12 can work at high frequencies offers another benefit: The drop of 1/f noise that is present in most low frequency strain gages.

Comparing to semiconductor gauges, metal films usually have lower temperature coefficient of resistivity (TCR), and lower temperature coefficient of gauge factor (TCGF). (See table 2.)

| Technology | GF | TCR (×10⁻⁶/K) | TCGF (×10⁻⁶/K) | Long-term stability |
|---|---|---|---|---|
| Metal-film | 2 | 10 × 10⁻⁶/K | 100 × 10⁻⁶/K | excellent |
| Thick-film | 3 ÷ 20 | 50 × 10⁻⁶/K | 300 × 10⁻⁶/K | very good |
| Semiconductor | 50 | 1500 × 10⁻⁶/K | 2000 × 10⁻⁶/K | good |

Metal thin film sensors can be operated under harsh circumstances, such as high temperatures and high pressure. They are also readily scalable without the depletion limit that exists in most doped semiconductors. The minimum dimension for a semiconductor to be conducting varies from a few nanometers to hundreds of nanometers, depending on the carrier density of the semiconductor. This problem becomes even more severe when dry etching damage is present. Such a process generally becomes obligatory at nanometer length scale.

The invention thus contemplates the use of thin and ultra-thin metal films for strain sensors. The very thin-films typically have thicknesses in the range of tens of nanometers and are characterized by a discontinuous metal island structure as shown in FIGS. 16a and 16b. A sketch of such a discontinuous metal island structure of the grains is shown in FIG. 16a when unstressed. The grain structure under stress is illustrated in FIG. 16b where the gap 54 in the grain structure has been widened by the stress applied to the film. This especially true when these metals are used in a nanowire geometry. The discontinuous type of gold thin film has demonstrated a gauge factor from 24 to 48, a much higher value than that of the continuous type which is about 2.6. For ultra thin films, it is not the thickness of thin metal film that determines the sensitivity of the discontinuous type of ultrathin film.

Pure metal such as Au, Cr, Ag, Pd, Ni, Pt, Mn and alloys, Au—Ni, NiCr, Bi—Sb, Ag—Ni, Cu—Ni, and Pt—Cr are used as materials of metal thin-film-type strain gauges. Their simplicity, reliability and ability to perform in a wide range of environmental conditions have made these gauges available in may shapes, patterns and configurations. The Table below summarizes the gauge factors of thin metal films that have been explored in literature.

| Material | Composition | GF |
|---|---|---|
| Cr | 100 | |
| Au | 100, continuous | 2.6 |
| Au | 100, discontinuous | 24.48 |
| Ag | 100, discontinuous | 45 |

-continued

| Material | Composition | GF |
|---|---|---|
| Pd | 100 | 2.5 |
| Pt | 100 | |
| Ni | 100 | 40 |
| Constantan | 45 Ni, 55 Cu | 2.1 |
| Ni-Ag | 35.50 Ni, Ag | |
| Karma | 74 Ni, 20 Cr, 3 Al, 3 Fe | 2.0 |
| Isoelastic | 36 Ni, 8 Cr, 0.8 Mo, 55.5 Fe | 3.6 |
| Nichrome V | 80 Ni, 20 Cr | 2.1 |
| Pt-W | 92 Pt, 8 W | 4.0 |
| Pd-Cr | 87 Pt, 13 Cr | |
| Armour D | 70 Fe, 20 Cr, 10 Al | 2.0 |

However, constructed at a comparably large scale, they have a lower sensitivity than nanowires 12 implemented according to the invention.

Figure 6:
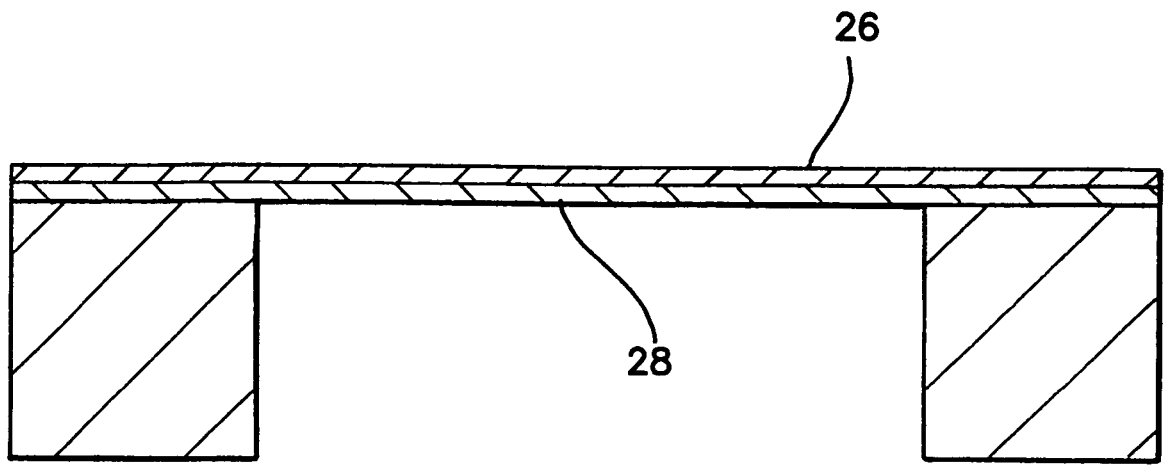
FIG. 6. Typical bimorph structure that is required for the construction of nanowire sensors.

Our choice of thin film metallic materials to construct nanowires 12 is largely dependent on the actual fabrication process and the conductivity of the metal. Many methods of deposition methods can be employed: evaporation, sputtering, CVD, etc. For embedded metal wires, the design is straightforward in the sense that only the surface strain is required to be measured. In the case of the free-standing metal nanowires, the fabrication is not trivial. Usually a bimorph structure has to be incorporated to avoid the compensation of tensile strain and compressive strain at the top surface 26 and bottom surface 28 of the suspended beam or wire 12 as shown in FIG. 6. The bottom layer 28 of the bimorph structure is usually insulating or has higher resistivity than the piezoresistor to gain maximum strain sensitivity. For thin film metal piezoresistors, the bottom layer 28 could be simply another higher resistive metal layer such as Au/Cr or a semiconductor such as Metal/Si, Metal/SiC, Metal/GaAs etc. or an insulating layer such as Metal SiO2, Metal/SiN, Metal/SiNO etc.

b. Si Based Nanowire Piezosensors

It is well known that piezoresistance of silicon can be used as a sensing element for mechanical sensors, such as diaphragm type pressure sensors. This is due to the excellent electrical and mechanical properties of silicon and due to the availability of integrated circuit compatible fabrication processes.

First consider the mechanical properties of silicon. For single crystal silicon of cubic structure, the Young's modulus E depends on the crystal orientation, $$E^{-1} = s_{11} - 2\left(s_{11} - s_{12} - \frac{1}{2}s_{44}\right)\Gamma \tag{10}$$

where $\Gamma = y_1^2 y_2^2 + y_2^2 y_3^2 + y_3^2 y_1^2$ and $y_1$, $y_2$ and $y_3$ are the direction cosines, and $s_{11}$, $s_{12}$ and $s_{44}$ are the matrix elements in the strain tensor. The resulting Young's moduli for silicon in the predominant crystallographic directions are given in Table 4.

| | Si <100> | Si <110> | Si <111> |
|---|---|---|---|
| E (GPa) | 166 | 170 | 190 |
| P (kg/m³) | 2333 | 2333 | 2333 |

In most case, the mechanical anisotropy of silicon is not significant and can be ignored in the sensor design. Piezoresistive coefficients are frequently used in semiconductor strain gauges. A piezoresistor responds to stress σ as, $$\frac{\Delta\rho}{\rho} = \pi_l \sigma \tag{11}$$

Where $\pi_l$, is the longitudinal piezoresistive coefficient. There also exists a transverse piezoresistive coefficient, usually denoted as $\pi_t$. Analogously to the modulus of elasticity, the piezoresistive coefficients are determined by $\pi_{11}$, $\pi_{12}$, and $\pi_{44}$ $$\pi_t = \pi_{11} - 2(\pi_{11} - \pi_{12} - \pi_{44})\Gamma \tag{12}$$

Coefficients for p-type and n-type silicon is given in the table below.

| | | $\pi_{11}$ [$10^{11}$ m²/N] | $\pi_{12}$ [$10^{11}$ m²/N] | $\pi_{44}$ [$10^{11}$ m²/N] |
|---|---|---|---|---|
| n-Si | (11.7 □cm) | −102.2 | 53.4 | −13.6 |
| p-Si | (7.8.7 □cm) | 6.6 | −1.1 | 138.1 |
| n-Ge | (9.9 □cm) | −4.7 | −5.0 | −137.9 |
| p-Ge | (15 □cm) | −10.6 | 5.0 | 46.5 |

Figure 7:
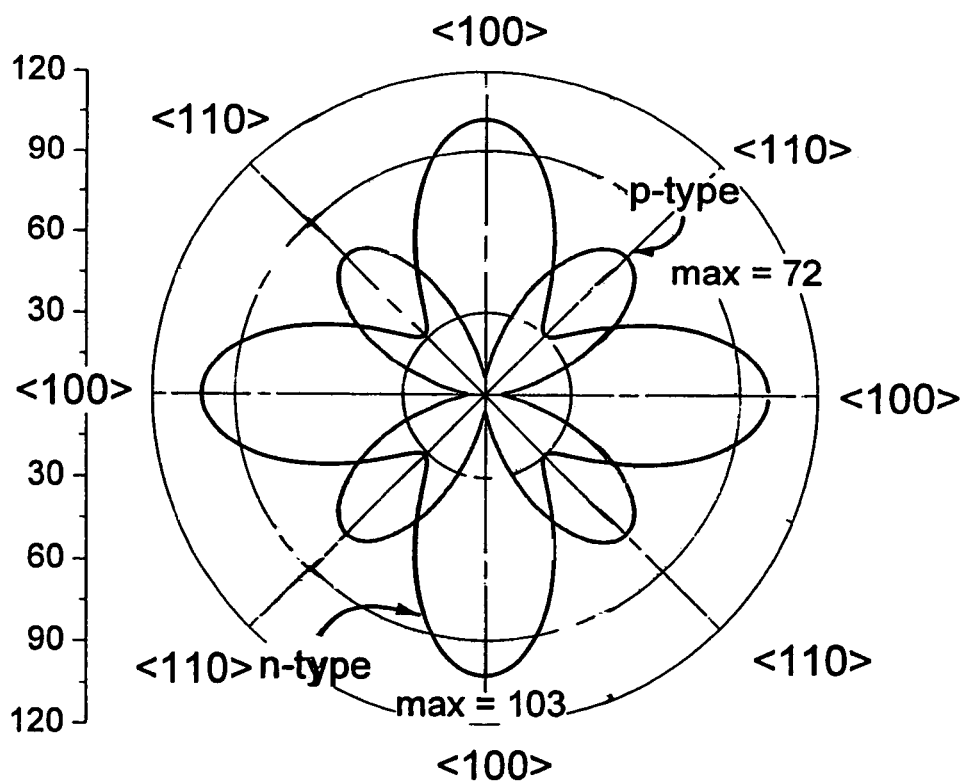
FIG. 7 is a polar graph of the room temperature piezoresistive coefficients of p-type and n-type silicon on the (100) plane.

FIG. 7 is a graph which shows the room temperature piezoresistive coefficients of both p-type silicon and n-type silicon in the (100) plane. It can be seen that p-type silicon has its maximum piezoresistive coefficient of $-72 \times 10^{-11}$ m²/N in the <110> direction; while n-type silicon has its maximum of $-103 \times 10^{-11}$ m²/N in the <100> direction. Although n-type silicon can achieve piezoresistive coefficients much higher than that of p-type silicon, all piezoresistive sensors fabricated to date, including pressure sensors, accelerometers, and AFM cantilevers are doped p-type. This is partially for historical reasons. Traditional MEMS's rely on wet etching of Si, such as TMAH and KOH etchants, which etch silicon preferentially to expose the (111) plane. Therefore the membrane edge of the front side is always in parallel to <110> direction, where p silicon has maximum piezoresistive coefficient while n silicon has minimum piezocoefficient. By using a deep reactive ion etching DRIE technique, nanowires or nanocantilevers 12 can be easily patterned and released along any chosen crystal orientation, therefore improving the piezoresistivity.

The difficulty in making ohmic contacts between metal and n-type silicon is another concern. But this limitation can be also overcome with current fabrication techniques, for example, Al contact deposition followed by ion-cleaning of the contact windows.

Both p-type and n-type germanium can be used as strain sensor. The piezocoefficients are listed in the Table above and plotted in FIG. 8. germanium wires have the benefits of higher conductivity and ease in making ohmic contacts.

c. SiC Piezoresistor

Silicon carbide has long been viewed as a potentially useful semiconductor for high-temperature applications due to its excellent electrical characteristics. Its wide bandgap (~3.0 eV), high-breakdown electric field ($2.5 \times 10^6$ Vcm⁻¹) and high electron saturation velocity ($2 \times 10^7$ cm/s) make it a superior candidate for electronic applications in a harsh environment. Added to these, SiC exhibits excellent thermal and mechanical properties at high temperatures and fairly high piezoresistive coefficients, a combination which makes it suitable for use as an electromechanical sensor.

d. Groups III-V Based Semiconductor Nanowire Piezosensors

I. The piezoresistive effect of GaAs and AlGaAs

It is generally known that GaAs electronic circuits have a higher tolerance in high temperature and high radiation environments than that of silicon integrated circuits. On the other hand, GaAs membranes can be easily obtained by selectively etching the GaAs/AlGaAs heterostructures. In addition, GaAs nanowires are compatible with integrated high electron mobility transistor (HEMT) amplifiers. This becomes extremely important when the impedance of the piezoresistive wires are significantly larger than the input resistance of the measurement circuits.

Figure 9:
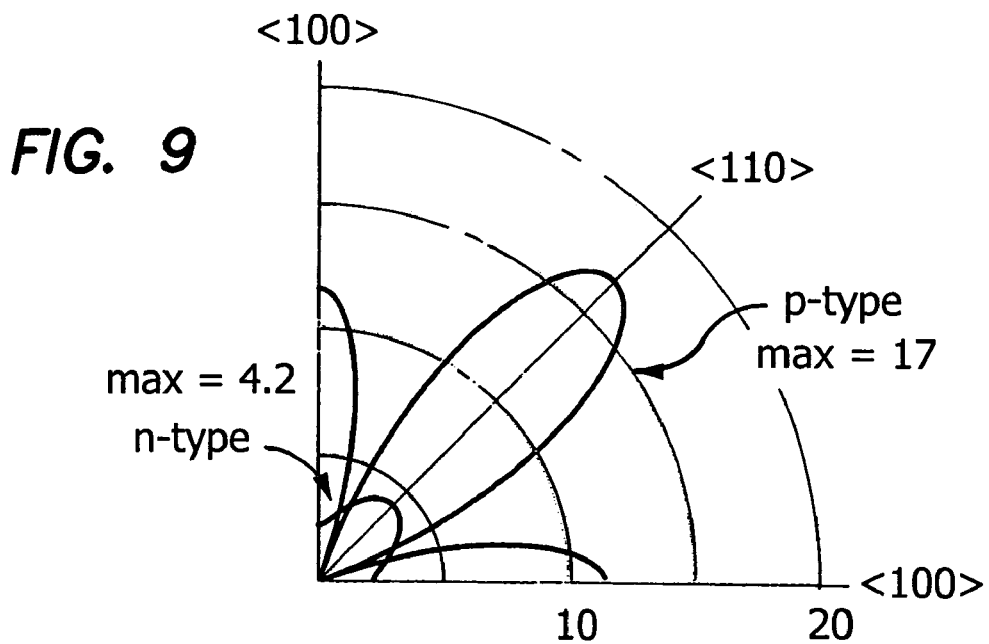
FIG. 9 is a polar graph of the absolute value of the piezoresistive constants of p-GaAs and n-GaAs for longitudinal piezoresistive coefficient $\pi$ in the (001) plane. The unit is $10^{-11}$ $Pa^{-1}$.

As discussed above, it has been well established that the piezoresistive effect of silicon is due to a directional dependent modulation of the average mobility in response to a uniaxially applied stress. But unlike Si, GaAs is a direct band semiconductor. This effect is not as high. FIG. 9 shows the a typical plot of the piezoresistive coefficients of p-type GaAs.

In addition to the effect of mobility changes, nonuniform stress distribution introduced into GaAs can produce piezoelectric charge densities and effectively shift the free charge densities originally established by doping. This effect becomes dominant for low doping level GaAs.

$Ga_xAl_{q-x}As$ with x lying between 25 and 40% can be used to develop highly sensitive strain gauges. Deep impurity states (DX centers) play a dominant role in the electrical conduction band. In contrast to shallow impurity states, which exhibit a relatively small pressure coefficient, the energy of DX states compared to the $\Gamma$ minimum of the conduction band decreases at a rate of 10 meV/kbar. As a consequence, one could observe a significant piezoresisitvity effect. In one embodiment, a device containing an optimized $Al_xGa_{1-x}As$ layer with thickness in the micrometer range, grown on semi-insulating GaAs substrate showed a gauge factor as high as 60.

II. The Piezoresistive Effect of AlGaN Based Materials

Solids with a large bandgap such as diamond or gallium nitride are prime candidates for a variety of sensor applications, particularly at high temperatures and in harsh environments. On the one hand, the large band gap ensures minimal problems due to unwanted optical or thermal generation of charge carriers. On the other hand, the strong chemical bonding between the constiuent atoms not only widens the forbidden gaps in the electronic density of states, but at the same time gives rise to a quite favorable mechanical, thermal and chemical stability of this class of materials.

Strong piezoelectricity provides unique possibilities for utilizing AlN—GaN materials in an emerging field of high temperature piezoelectronics. The piezoelectric effect plays an important role in GaN layers, AlGaN—GaN, AlN—GaN—InN heterostructures and quantum wells. Strain-induced electric fields can significantly modify the electrical properties of GaN-based devices by affecting the free carrier concentration.

High dynamic piezoresistive effect with a gauge factor of about 70 has been reported in n-type GaN layers. A large static gauge factor of about 50 was measured in GaN/AlN/GaN semiconductor-insulator-semiconductor structures. In AlN—GaN short range superlattices, it has been demonstrated that GF can reach 90, which is close to GFs of silicon diaphragms.

The piezoresistivity of $Al_xGa_{1-x}N$ layers with different Al contents and electron concentration have been investigated in the prior art. A strong increase of the gauge factor with increasing Al content is observed. The corresponding value is negative and its absolute value increases from 3.5 to 25.8 if the Al concentration is increased from x=0 to 0.35. In addition, a remarkably high gauge factor of −85 is observed for modulation doped AlGaN/GaN high electron mobility transistors containing a polarization induced two-dimensional electron gas.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A device, comprising:
   a cantilever;
   a metal thin film piezoresistor located on the cantilever; and a detector which is adapted to measure a resistance change in the piezoresistor in response to a force applied to the cantilever;

wherein:
the cantilever comprises a biofunctionalized cantilever;
the metal thin film piezoresistor is located adjacent to a base of the cantilever; and
the detector is adapted to detect binding of a biological analyte to the cantilever.

2. The device of claim 1 wherein the cantilever comprises a notched nanocantilever and the metal thin film piezoresistor is located on arm portions of the nanocantilever adjacent to the notch.

3. The device of claim 1 wherein the detector is adapted to detect binding of the biological analyte to the cantilever from a measurement of the resistance change in the piezoresistor.

4. The device of claim 1 wherein the cantilever comprises an inorganic material cantilever.

5. The device of claim 4 wherein the cantilever comprises an insulating inorganic cantilever.

6. The device of claim 5 wherein the cantilever comprises a silicon nitride, a silicon oxynitride or a silicon oxide cantilever.

7. The device of claim 1 wherein the cantilever comprises a semiconductor cantilever.

8. The device of claim 1 wherein the metal thin film comprises a pure metal composition selected from the group consisting of Au, Cr, Ag, Pd, Ni, Pt, or Mn, or alloys selected from the group consisting of Au—Ni, NiCr, Bi—Sb, Ag—Ni, Cu—Ni, or Pt—Cr.

9. The device of claim 1 wherein the thin metal film is located on a surface of the cantilever.

10. The device of claim 1 where the thin metal film comprises a film with a thickness on the order of tens of angstroms or less.

11. A measurement method, comprising:
providing a cantilever and a metal thin film piezoresistor located on the cantilever;
stressing the cantilever with a force having a transverse component; and
measuring a resistance change in the piezoresistor in response to the transverse component of the force applied to the cantilever;
wherein:
the cantilever comprises a biofunctionalized cantilever;
the metal thin film piezoresistor is located adjacent to a base of the cantilever; and
the step of stressing the cantilever comprises binding of a biological analyte to the cantilever.

12. The method of claim 11 further comprising detecting binding of the biological analyte to the cantilever from the step of measuring the resistance change.

13. The method of claim 11 wherein the cantilever comprises an inorganic material cantilever.

14. The method of claim 13 wherein the cantilever comprises an insulating inorganic cantilever.

15. The method of claim 14 wherein the cantilever comprises a silicon nitride, a silicon oxynitride or a silicon oxide cantilever.

16. The method of claim 11 wherein the cantilever comprises a semiconductor cantilever.

17. The method of claim 11 wherein the metal thin film comprises a pure metal composition selected from the group consisting of Au, Cr, Ag, Pd, Ni, Pt, or Mn, or alloys selected from the group consisting of Au—Ni, NiCr, Bi—Sb, Ag—Ni, Cu—Ni, or Pt—Cr.

18. The method of claim 11 wherein the thin metal film is located on a surface of the cantilever.

19. The method of claim 11 where the thin metal film comprises a film with a thickness on the order of tens of angstroms or less.

20. The method of claim 11 wherein the cantilever comprises a notched nanocantilever and the metal thin film piezoresistor is located on arm portions of the nanocantilever adjacent to the notch.

21. The method of claim 11 wherein the step of measuring the resistance change comprises measuring the resistance change dynamically over time to detect a dynamic motion of the cantilever as a function of time.

22. The method of claim 21 further comprising detecting binding of the biological analyte to the cantilever from the step of measuring the resistance change by using a resonant frequency of the cantilever.

23. The method of claim 11 further comprising obtaining a frequency spectrum of the cantilever.

24. The device of claim 1 wherein the detector is adapted to measure the resistance change dynamically over time to detect a dynamic motion of the cantilever as a function of time.

25. The device of claim 24 wherein the detector is adapted to detect binding of the biological analyte to the cantilever from a measurement of the resistance change in the piezoresistor by using a resonant frequency of the cantilever.

26. The device of claim 1 wherein the detector is adapted to obtain a frequency spectrum of the cantilever.

* * * * *